United States Patent [19]

Schachter et al.

[11] Patent Number: 4,840,894
[45] Date of Patent: Jun. 20, 1989

[54] METHOD FOR DETECTING A MARKER FOR ESSENTIAL HYPERTENSION AND DIAGNOSTIC USE THEREOF

[75] Inventors: David Schachter; Szloma Kowarski, both of Bronx; Lisa A. Cowen, New York, all of N.Y.; Richard E. Abbott, Englewood, N.J.

[73] Assignee: The Trustees of Columbia University in the City of New York, New York, N.Y.

[21] Appl. No.: 835,898

[22] Filed: Mar. 4, 1986

[51] Int. Cl.[4] ............... G01N 33/53; G01N 33/543; G01N 33/555; G01N 33/577
[52] U.S. Cl. ..................... 435/7; 435/172.3; 435/240.27; 436/63; 436/174; 436/519; 436/520; 436/529; 436/533; 436/534; 436/548; 436/804; 436/811; 530/350; 530/387; 935/110
[58] Field of Search ............ 435/7, 172.2, 240.27; 436/529, 548, 804, 810, 811, 533, 534, 63, 174; 530/350, 387; 935/110

[56] References Cited

U.S. PATENT DOCUMENTS 4,321,120 3/1982 Nardi .
4,402,872 9/1983 Bohn .

OTHER PUBLICATIONS

Kowarski, S. Cowen, L., and Schachter, D., P.N.A.S. USA, 83, pp. 1097–1100 (Feb. 1986).
Kowarski, S., Cowen, L. A., and Schachter, D. Fed. Proc. 44, 4, pp. 1127 (1985).
Kowarski, S. and Schachter, D., J. Biolog. Chem. 255, pp. 10834–10840 (1980).
Cloix, J. et al., Hypertension, 5(1), 128–134, (1983).
Diesterhaft, M., Biochem. Biophys. Res. Comm., 125(3), 888–894, (Dec. 28, 1984).
Van de Voorde, A. et al., Biochem. Biophys. Res. Comm., 111(3), 1015–1021, (Mar. 29, 1983).
Chemical Abstracts, 97:89899y (1982).
Kohler, G. et al., Nature, 256, 495–497, (Aug. 7, 1975).
Votila, M. et al., Molecular Immunology, 17, 791–794, (1980).

Primary Examiner—Sidney Marantz
Attorney, Agent, or Firm—John P. White

[57] ABSTRACT

A method for detecting the presence in a human of an integral membrane calcium-binding protein associated with essential hypertension which comprises isolating tissue from a human, treating the tissue to obtain integral membrane proteins, contacting the proteins thus obtained with a first antibody molecule which binds to the integral membrane calcium binding protein to form a detectable protein-antibody complex, and detecting the complex so formed.

Further, methods for quantitatively determining the amount of an integral membrane calcium-binding protein and the messenger RNA encoding said protein, diagnostic methods for identifying individuals predisposed to essential hypertension, and protein and messenger RNA associated with said hypertension.

34 Claims, No Drawings

METHOD FOR DETECTING A MARKER FOR ESSENTIAL HYPERTENSION AND DIAGNOSTIC USE THEREOF

The invention described herein was made with government support under grants numbered AM01483, HL16851, and AM21238 from the National Institutes of Health, United States Department of Health and Human Services. The government has certain rights in this invention.

BACKGROUND OF THE INVENTION

Throughout this application various publications are referenced by a number within parentheses. Full citations for these publications may be found at the end of the specification immediately preceding the claims. The disclosures of these publications in their entireties are hereby incorporated by reference into this application in order to more fully describe the state of the art to which this invention pertains.

Arterial hypertension is a condition of sustained elevated systemic arterial blood pressure. The minimum level of systemic arterial pressure considered to be hypertensive has been arbitrarily set at 140/90 mm Hg. While hypertension usually involves elevations in mean and pulse pressures, the rise in diastolic pressure is clinically regarded as the critical criterion, suggesting that hypertension is due primarily to an increased peripheral resistance.

Hypertension is a serious cardiovascular disease. It is responsible for approximately 10 percent of deaths in people over 50 years of age. However, many of the people in this group may have blood pressures as high as 170/90 without displaying any symptoms of hypertension, and approximately 75 percent of these individuals die of diseases which may have caused their hypertension.

Hypertension is an important clinical disorder because it leads to organic alterations of the heart, brain, kidneys, and arterial vasculature. In hypertension, the heart must pump blood into the arterial systems against a higher than normal level of pressure. Consequently, the heart must perform additional work, and therefore it hypertrophies. Hypertrophy may eventually lead to myocardial failure. The cerebral vasculature does not possess the tissue support found in other regions of the body, and cerebral hemorrhages in hypertensives are not uncommon. Renal insufficiency, which results from arterionephrosclerosis, is a frequent complication of hypertension. The continuous added stress placed upon the arterial system in hypertension ultimately leads to sclerosis of the arterial wall. This alteration of the vascular system may modify tissue blood flow and thereby cause disruption of tissue function.

In approximately 30 percent of the cases of hypertension, the elevated blood pressure is a clinical sign of specific disease, e.g., renal disease, and not a disease entity in itself. Such conditions of elevated blood pressures are referred to as secondar hypertension. In the remaining 70 percent the development of hypertension cannot be attributed to any known origin and probably represents a specific disease state.

Essential hypertension refers to this sustained elevation in systemic arterial blood pressure for which there is no discernible origin. The hypertension may be "benign" in that it may develop slowly and progressively over many years, or it may be "malignant" and develop rapidly in a brief period of time. Attempts to identify the cause of essential hypertension have been fruitless. After exclusion of hypertension due to renal disease, adrenal dysfunction, or cardiovascular and neurogenic alterations, no reasonable explanation is obvious at this time.

The spontaneously hypertensive rat (1) exhibits features observed in human essential hypertension (2-5) and has evoked considerable interest as a model of the human disease. Abnormalities of calcium binding or translocation, for example, have been detected both in the genetically-determined rat disorder (2,6-15) and in the human disease (2,5,16). These calcium abnormalities are of particular significance because they may underlie the pathogenesis of the hypertension (6-12, 14-16).

In spontaneously hypertensive rats (SHR) the alterations include reduced binding of calcium to the plasma membranes of various cell types (2,13-15); impaired flux of calcium out of the cystosol via active transport dependent on adenosine triphosphate (7-12, 14); and increased passive permeability of erythrocyte membranes to the cation (14). These changes are expected to increase the ionized $Ca^{2+}$ concentration of the cytosol and in the case of the excitable cells to enhance vascular smooth muscle tone and the peripheral resistance of the blood circulation (15). In human essential hypertension the binding of calcium to erythrocyte membranes is decreased as compared to normotensive controls (2) and the concentration of ionized $Ca^{2+}$ within blood platelets is elevated (16).

The foregoing evidence points to a genetically-determined alteration in SHR of a membrane component responsible for binding calcium. The isolation from rat intestinal mucosa of an integral membrane calcium binding protein, IMCAL, which binds calcium with relatively high affinity and is regulated by vitamin D and the level of dietary calcium has been described (17-19). Evidence that the calcium binding activity of intestinal IMCAL is closely correlated with the capacity of the mucosa to transport the cation (17, 20) suggests that IMCAL is a component of the membrane mechanism which mediates or regulates calcium translocation. Immunoassays which utilized polyclonal antisera or a mouse monoclonal antibody to IMCAL have demonstrated that the protein is present in many rat tissues (19). Because decreases in IMCAL content might account for the reduction in calcium binding to membranes of SHR, immunoassays to tissues of SHR, Wistar Kyoto controls and Sherman strain controls were evaluated. The results demonstrate that the IMCAL content of at least seven SHR tissues is significantly lower than that of the normotensive control strain. Moreover, this change is observed in young 4-week old SHR, prior to development of hypertensive pressure levels.

Because of the long term detrimental effects of essential hypertension, it would be beneficial to have a method for identifying the relative amounts of IMCAL present in the tissues, since decreased amounts of IMCAL are expected to lead to essential hypertension in human subjects as they do in SHR.

Further because of the prevalence of essential hypertension in the human population, it would be beneficial to have a diagnostic method for identifying individuals predisposed to essential hypertension.

Such a method would have far reaching economic importance as a simple and accurate diagnostic test, and would also stimulate that segment of the pharmaceutical market producing drugs for anticipatory treatment of predisposed patients.

Finally, isolation of protein or messenger RNA associated with essential hypertension would allow research into new pharmaceuticals for treatment of essential hypertension.

SUMMARY OF THE INVENTION

The present invention provides a purified integral membrane calcium-binding protein having a molecular weight of about 200,000 daltons in non-denaturing deweight of about 200,000 dalt tergents and of about 20,500 daltons in sodium dodecyl sulfate polyacrylamide gels, a blocked amino terminus, an isoelectric point of about 4.5 and an affinity constant for the complexation of calcium of about 2.4 micromolar.

A monoclonal antibody directed against the protein of the present invention has been prepared and designated RC2B6/1D1 produced by hybridoma cell line ATCC No. HB9317.

A method of preparing the protein of the present invention comprises:
 a. extracting membrane proteins from animal tissue to form a membrane protein extract;
 b. solubilizing the extracted membrane proteins; and
 c. recovering thepprotein of claim 1 from the solubilized membrane proteins by immunoprecipitation or immunoaffinity chromatography with monoclonal antibody RC2B6/1D1.

The invention concerns a method for detecting the presence in a human of an integral membrane calcium-binding protein (IMCAL) associated with essential hypertension. The method comprises isolating tissue from a human, treating the tissue to obtain integral membrane proteins, contacting the proteins thus obtained with a unique first antibody molecule which binds specifically to the integral membrane calcium binding protein to form a detectable protein-antibody complex, and detecting the complex so formed.

The detecting may comprise a first antibody labeled with a detectable marker or a first antibody bound to a matrix. The complex may produce a detectable product of an enzymatic reaction or may be detected by autoradiography.

The detecting may also comprise a second antibody molecule which binds the protein-first antibody complex. The second antibody may be labeled with a detectable marker, and the complex may be detectable by autoradiography or colorimetry.

The invention also concerns a method for quantitatively determining the amount in a human of an integral membrane calcium-binding protein (IMCAL) associated with essential hypertension. The method comprises isolating tissue from a human, treating the tissue to obtain integral membrane proteins, contacting the proteins thus obtained with an antibody molecule that binds to the integral membrane calcium binding protein to form an identifiable protein-antibody complex and quantitatively determining the amount of complex so formed.

The invention also concerns a method for quantitatively determining the amount in a human of messenger ribonucleic acid (mRNA) encoding an integral membrane calcium-binding protein associated with essential hypertension. The method comprises isolating the tissue from a human, treating the tissue to obtain the mRNA, contacting the mRNA thus obtained with a cDNA probe that binds to the mRNA encoding the integral membrane calcium-binding protein to form an identifiable mRNA-antibody complex and quantitatively determining the amount of complex so formed.

The invention also concerns a diagnostic method for identifying individuals predisposed to essential hypertension. The method comprises isolating tissue from the individual, treating the tissue to obtain integral membrane proteins, contacting the proteins thus obtained with an antibody molecule that binds to an integral membrane calcium binding protein to form an identifiable protein-antibody complex, quantitatively determining the amount of complex so formed and comparing the amount with the amount of protein bound from tissues of a normal individual, a significant decrease in the amount bound indicating a predisposition to the disease.

The invention also concerns a method for quantitatively determining the amount in a human of messenger ribonucleic acid (mRNA) encoding an integral membrane cal- cium-binding protein associated with essential hypertension. The method comprises isolating the tissue from a human, treating the tissue to obtain the mRNA, contacting the mRNA thus obtained with a cDNA probe that binds to the mRNA encoding the integral membrane calcium-binding protein to form an identifiable mRNA-antibody complex and quantitatively determining the amount of complex so formed.

Further, the invention concerns an integral membrane calcium-binding protein characterized by having a molecular weight of about 20,500 daltons on a sodium dodecyl sulfate-polyacrylamide gel and by being associated with essential hypertension.

Finally, the invention concerns an antibody molecule produced by contacting the immune system of an animal with an integral membrane calcium-binding protein, said protein associated with essential hypertension and having a molecular weight of about 20,500 daltons on a sodium dodecyl sulfate-polyacrylamide gel, and isolated therefrom.

DETAILED DESCRIPTION OF THE INVENTION

The present invention provides a purified integral membrane calcium-binding protein having a molecular weight of about 200,000 daltons in non-denaturing detergents and of about 20,500 daltons in sodium dodecyl sulfate polyacrylamide gels, a blocked amino terminus, an isoelectric point of about 4.5 and an affinity constant for the complexation of calcium of about 2.4 micromolar.

A monoclonal antibody directed against the protein of the present invention has been prepared and designated RC2B6/1D1 produced by hybridoma cell line ATCC No. HB9317.

A method of preparing the protein of the present invention comprises:
 a. extracting membrane proteins from animal tissue to form a membrane protein extract;
 b. solubilizing the extracted membrane proteins; and
 c. recovering the protein of claim 1 from the solubilized membrane proteins by immunoprecipitation or immunoaffinity chromatography with monoclonal antibody RC2B6/1D1.

A method for detecting the presence in a human of an integral membrane calcium-binding protein associated with essential hypertension is disclosed. The method comprises isolating tissue from a human, treating the tissue to obtain integral membrane proteins, contacting the proteins thus otained with a first antibody molecule which binds to the integral membrane calcium binding protein to form a detectable protein-antibody complex, and detecting the complex so formed.

Tissues most useful for the practice of this invention are erythrocyte membrane or placenta. However, intestine, kidney, bone, brain, heart, testis, spleen, skeletal muscle, liver or any other convenient tissue may also be used.

The integral membrane proteins may be isolated by a variety of techniques well known to those skilled in the art. The isolation may include steps such as washing, centrifugation, lysis under hypoosmotic conditions, scraping, and homogenization; various other steps may also be employed. Centrifugation time and force, homogenization time and speed, the constitution and concentration of various buffers, or various other parameters may be varied, as is well known in the art, all of which lead to the isolation of integral membrane proteins.

In the presently preferred embodiment, the first antibody is either a monoclonal or polyclonal antibody. Further, the first antibody may be bound to a support matrix, such as agarose, sepharose, the wall of a tube, a bead or any of a number of support matrices.

The second antibody of the preferred embodiment is a polyclonal antibody and the attached detectable marker is an enzyme such as horseradish peroxidase. However, detectable markers attached to the first and second antibodies may be radioactive labels, e.g. $^{125}I$, or any of a variety of colorometric or fluorometric markers or may be the product of other enzymatic reactions.

In the preferred embodiment, the first antibody is contacted with an integral membrane protein, forming a protein-first antibody complex. This complex is then contacted with the second detectable antibody labeled with an enzyme, horseradish peroxidase. The second complex is then detected by enzymatic reaction with an appropriate substrate, e.g. o-phenylenediamine, to form a detectable product.

In another embodiment, the second antibody is labeled with $^{125}I$ and the second complex is detected by autoradiography. In another embodiment, the second complex may form a precipitate and may be detectable by visual observation.

A method is disclosed for quantitatively determining the amount in a human of an integral membrane calcium-binding protein associated with essential hypertension. The method comprises isolating tissue from a human, treating the tissue to obtain integral membrane proteins, contacting the proteins thus obtained with an antibody molecule that binds to the integral membrane calcium binding protein to form an identifiable protein-antibody complex and quantitatively determining the amount of complex so formed.

As described hereinabove, presently preferred tissues are erythrocyte membrane or placenta, although intestine, kidney, bone, brain, heart, testis, spleen, skeletal muscle, liver or other tissues may be used.

The proteins are isolated using a combination of steps including, but not limited to, washing, centrifugation, hypoosmotic lysis, scraping, homogenization or any other useful steps.

First antibody molecules are preferably monoclonal, although polyclonals or one of a selected combination may also be used. Second antibody molecules are also either monoclonal or polyclonal and will be labeled with a detectable marker, e.g. $^{125}I$ or horseradish peroxidase.

Detectable markers may also be other radioactive labels, e.g. cobalt, or any of a variety of colorometric or fluorometric markers or may be the product of an enzymatic reaction.

In the presently preferred embodiment, the first antibody molecule is contacted with the integral membrane protein to from a protein-first antibody complex. The complex is then contacted with the second detectable antibody labelled with an enzyme to form a second detectable complex. In another embodiment, the second antibody is labeled with $^{125}I$ or another detectable component.

The amount of second detectable complex is then quantitatively determined, by methods known to those skilled in the art, and is compared to the amount from a normal individual, e.g. an individual with no predisposition to essential hypertension, the presence of a significantly different amount indicating a predisposition to the disease.

Further, a method is disclosed for quantitatively determining the amount in a human of messenger ribonucleic acid (mRNA) encoding an integral membrane calcium-binding protein associated with essential hypertension. The method comprises isolating the tissue from a human, treating the tissue to obtain the mRNA, contacting the mRNA thus obtained with a cDNA probe that binds to the mRNA encoding the integral membrane calcium-binding protein to form an identifiable mRNA-antibody complex and quantitatively determining the amount of complex so formed.

Presently preferred tissue is placenta, although intestine, kidney, bone, brain, heart, testis, spleen, skeletal muscle, liver or other tissues may be used.

The mRNA is isolated using a combination of steps including, but not limited to, washing, centrifugation, hypoosmotic lysis, scraping, homogenization, isolation of poly(A)-mRNA by oligo-dT column, or any other useful steps.

The cDNA probes are radioactive and the bound complex is estimated by counting in a radiation spectrometer, by autoradiography or by other methods known to those skilled in the art.

Detectable markers may be other radioactive labels, e.g. cobalt, or any of a variety of colorometric or fluorometric markers or may be the product of an enzymatic reaction.

In the presently preferred embodiment, the radioactive cDNA probe is contacted wit the mRNA to form a radioactive complex which may be quantified.

A diagnostic method is described for identifying individuals predisposed to essential hypertension. The method comprises isolating tissue from the individual, treating the tissue to obtain integral membrane proteins, contacting the proteins thus obt ained with an antibody molecule that binds to an integral membrane calcium binding protein to form an identifiable protein antibody complex, quantitatively determining the amount of complex so formed and comparing the amount with the corresponding amount observed with tissues of a normal individual, a significant decrease in the amount of antibody bound indicating a predisposition to the disease.

As described hereinabove, presently preferred tissues are erythrocyte membrane or placenta, although intestine, kidney, bone, brain, heart, testis, spleen, skeletal muscle, liver or other tissues may be used.

The proteins are isolated using a combination of steps including, but not limited to, washing, centrifugation, hypoosmotic lysis, scraping, homogenization or any other useful steps.

First antibody molecules are either monoclonal or polyclonals or one of a selected combination may also be used. Second antibody molecules may be labeled with a detectable marker, e.g. $^{125}I$ or horseradish peroxidase.

Detectable markers may also be other radioactive labels, e.g. cobalt, or any of a variety of colorometric or fluorometric markers or may be the product of an enzymatic reaction.

In the presently preferred embodiment, the first antibody molecule is contacted with the integral membrane protein to from a protein-first antibody complex. The complex is contacted with the second detectable antibody to form a second detectable complex. The second antibody is labeled with an enzyme, e.g. horseradish peroxidase, and the second complex is contacted with an appropriate substrate, e.g. o-phenylenediamine, to form a detectable product. The second antibody can also be labelled radioactively.

The amount of second detectable complex is then quantitatively determined, by methods known to those skilled in the art, and is compared to the amount from a normal individual, e.g. an individual with no predisposition to essential hypertension, the presence of a significantly different amount indicating the predisposition to the disease.

Finally, a diagnostic method is described for identifying individuals predisposed to essential hypertension. The method comprises isolating tissue from the individual, treating the tissue to obtain the mRNA, contacting the mRNA thus obtained with a radioactive cDNA probe which binds to the mRNA encoding an integral membrane calcium-binding protein associated with essential hypertension to form an identifiable mRNA-cDNA complex, quantitatively determining the amount of complex so formed, and comparing that amount with the amount of mRNA-cDNA complex formed by tissues of a normal individual, a significant decrease in the amount bound indicating a predisposition to the disease.

Presently preferred tissue is placenta, although intestine, kidney, bone, brain, heart, testis, spleen, skeletal muscle, liver or other tissues may be used.

The mRNA is isolated using a combination of steps including, but not limited to, washing, centrifugation, hypoosmotic lysis, scraping, homogenization, isolation of poly(A)-mRNA by oligo dT-column, or any other useful steps.

Specific cDNA probes for the mRNA are labeled radioactively with $^{32}P$ or other radioactive elements. The complex of mRNA and cDNA formed is quantified by estimation of the radioactivity in a radiation spectrometer, or by autoradiography, or by other methods known to those skilled in the art. The amount of specific mRNA-cDNA complex is compared to the corresponding amount from a normal individual, an individual with no family history of predisposition to essential hypertension. The observation of a significantly decreased amount from normal indicates the predisposition to the disease.

Materials and Methods

Properties of IMCAL

IMCAL has been identified and isolated from both rat and human tissues. It has been isolated from rat duodenal mucosa and purified to electrophoretic homogeneity. IMCAL has also been partially purified from human placenta.

When extracted with neutral detergents from rat duodenal mucosa the undenatured protein has a molecular weight of 200,000 daltons by gel filtration. Treatment with sodium dodecylsulfate (SDS) yields a monomer of MW 20,500 daltons. Human placental IMCAL has the identical molecular weight as the rat protein, based on gel electrophoresis of the undenatured and the SDS-treated preparations.

The amino acid composition of rat IMCAL has been determined (17), and it is rich in aspartic and glutamic acids. The amino acid composition is unique and distinguishes IMCAL from other calcium binding proteins such as CaBP (25), calmodulin or parvalbumin. The amino terminus of IMCAL is blocked. The isoelectric point of rat IMCAL is approximately 4.5. The affinity constant for complexation of calcium by IMCAL has been estimated as $2.4\pm0.3$ micromolar.

The capacity of rat IMCAL to bind various cations has been examined by competition studies. The per cent inhibition of $^{45}Ca$ binding ($Ca^{2+}$ present at 4 micromolar) by 40 micromolar competing cation is as follows: $Pb^{2+}$, 97.9%; $La^{3+}$, 89.5%; $Cd^{2+}$, 78.6%; $Tb^{3+}$, 74.6%; $Cu^{2+}$, 62.9%; $Zn^{2+}$, 59.3%; $Mn^{2+}$, 44.2%; $Sr^{2+}$, 39.9%; $Ba^{2+}$, 34.3%; $Hg^{2+}$, 21.7%; and $Mg^{2+}$, 5.1.

IMCAL tends to aggregate in aqueous solution. Detergents must be present to maintain solubility of this membrane protein.

Unique polyclonal (rabbit) and monoclonal (mouse) antibodies to rat IMCAL have been prepared. The antibodies do not cross react significantly with calmodulin, parvalbumin or CaBP (25).

Immunochemical assays show that IMCAL is present in at least 14 tissues of the rat. The amount of tissue IMCAL is much greater in vitamin D-treated as compared to vitamin D-deficient rats, and it is greater in animals on a low calcium diet as compared to a high calcium diet.

Human IMCAL cross reacts immunochemically with the anti-rat IMCAL antibodies. Immunoassays have demonstrated human IMCAL in erythrocyte ghost membranes, blood platelets and placenta.

Animals and tissues. Albino male Spontaneously Hypertensive Rats (Tac:N(SHR)fBR) and Wistar Kyoto controls (Tac:N(WKY)fBR) were obtained from Taconic Farms, Inc. (Germantown, NY). Two age groups were studied: 4–5 weeks old (weight range 58–80 g) and 8–9 weeks old (weight range 161–195 g). Systolic arterial blood pressure was estimated by tail plethysmography; mean values ± SE for the SHR and Wistar Kyoto groups, respectively, were $130\pm3$ mm Hg and $113\pm3$ mm Hg at 4–5 weeks of age and $172\pm3$ mm Hg and $123\pm4$ mm Hg at 8–9 weeks. Sherman strain controls were purchased from Camm Research Institute (Wayne, N.J.) and all the animals were maintained on a nutritionally complete pellet diet (Camm Maintenance Rodent Diet; 0.9% Calcium; 0.8% phosphate) with water ad libitum. Rats were deprived of food for 18–24 hours to empty the upper intestine; the fast did not empty the cecum. Thereafter, the animals were killed by rapid stunning and exsanguination. Blood from adult human patients and controls was also collected by usual methods.

Blood was heparinized, the erythrocytes were isolated by centrifugation and washed twice with 0.145M NaCl -5 mM KCl, and ghost membranes (white to light pink) were prepared by osmotic lysis in 8 mM sodium phosphate of pH 7.4 as previously described (21). Intestinal segments were rinsed with ice-cold 0.145M NaCl - 5 mM KCl and the mucosa was scraped from the underlying coats (2). Other solid tissues were immediately immersed and rinsed in the ice-cold 0.145M NaCl - 5 mM KCl to remove move gross blood. Further manipulations were at 2°-5° C. Mucosal scrapings were homogenized in 10 volumes of a buffer solution (13 mM Tris buffer of pH 7.4 containing 119 mM NaCl plus 4.7 mM KCl) for 25 seconds in a Vir-Tis homogenizer (Virtis Co., Gardiner N.Y.) set at 70% of full scale. Other solid tissues were homogenized similarly, except that the duration was 1 min at full speed. Each homogenate was centrifuged at 100,000 x g for 2 hours and the pellet (total particulate fraction) was suspended in 8 ml of the homogenizing buffer to provide the starting material for the immunoassays below. The protein content of these suspensions ranged from 3–10 mg/ml as estimated by a modified Lowry method (22) using bovine serum albumin as the reference standard.

Antibodies. Denaturation of IMCAL with sodium dodecyl sulfate (SDS) yields a monomer of molecular weight of 20,500 (17). The SDS-monomer was purified by polyacrylamide slab gel electrophoresis and the gel band excised and used as antigen to immunize rabbits (23). Specificity of the antisera was assessed by an electroblotting technique. A crude, soluble preparation of duodenal mucosal proteins obtained by Sephadex G-150 gel filtration (17) was treated with 2% SDS for 3 min at 100° C., and the resulting SDS-proteins were resolved by electrophoresis in a discontinuous (4%/12%) SDS-polyacrylamide slab gel. The resolved proteins were transferred to a sheet of nitrocellulose by electroblotting (24) in a Bio-Rad (Richmond, CA) Trans-Blot apparatus. Strips of the nitrocellulose were treated with rabbit anti-serum or control serum and after appropriate washing bound antibody was localized using an affinity-purffied goat anti-rabbit IgG antibody conjugated with horseradish peroxidase (Kirkegaard & Perry Laboratories, Gaithersberg, MD) and 3,3'-diaminobenzidine as substrate for the staining reaction. One rabbit antiserum was essentially monospecific for the IMCAL SDS-monomer, whereas a second antiserum yielded predominant staining of the IMCAL band (greater than 90%) plus some staining of a higher molecular weight band (approximately 100,000 daltons). To ensure specificity of the immunoassay for the IMCAL SDS-monomer a quantitative electroblotting procedure was developed as described below.

A monoclonal antibody to native IMCAL was prepared by growth of a mouse hybridoma clone (RC2B6/1D1). Hybridoma cell line RC2B6/1D1 was deposited with the American Type Culture Collection (ATCC), 12301 Parklawn Drive, Rockville, Md. 20852 and designated ATCC Accession No. HB9317. This deposit was made pursuant to the Budapest Treaty On the International Recognition of the Deposit of Microorganisms For the Purposes of Patent Procedure. The cells were grown in suspension culture and approximately $5-10 \times 10^6$ cells were injected intraperitoneally into BALB/c mice primed with pristane. Ascitic fluid was harvested after 2-weeks and the IgG fraction isolated by column chromatography on protein A-Sepharose (Pharmacia P-L Biochemicals, Milwaukee, Wis.) Two procedures were used to demonstrate the specificity of the antibody for rat IMCAL. A crude mixture of rat duodenal membranes was solubilized by extraction with 1-butanol and the extract resolved by electrophoresis in slab polyacrylamide gels (non-denaturing) as previously described (17), alongside lanes of authentic rat IMCAL. The gels were transferred to nitrocellulose by electroblotting and one band of immunoreactive IMCAL was observed in the crude fractions using the mouse monoclonal primary antibody and a goat anti-mouse peroxidase-linked secondary antibody (Boehringer Mannheim; Indianapolis, Ind.) as described above In the second procedure the mouse monoclonal antibody isolated from ascitic fluid was immobilized by coupling to activated CH Sepharose 4B (Pharmacia) and an immunoaffinity column prepared. A crude mixture of butanol-solubilized duodenal membrane proteins (see above) was equilibrated in the column and, after extensive washing, bound proteins were eluted with 50 mM sodium acetatecitrate buffer of pH 2.6. The fractions were treated with 2% SDS as described above and resolved by SDS-polyacrylamide gel electrophoresis on 4–30% continuous gradient slab gels (Pharmacia). Staining with Coomassie brilliant blue revealed only the IMCAL band.

Immunoassay with polyclonal antiserum. The IMCAL content of the total particulate fraction was quantified by an electrophoretic blotting method. For the assay purified rat IMCAL (17) was labeled with 125I by means of a solid phase lactoperoxidase-glucose oxidase reagent mixture (Bio-Rad "Enzymo-beads") to a specific radioactivity of approximately 650 cpm/ng. A sample of tissue particulate containing 100 micrograms of protein was mixed with 17 ng of [$^{125}$I] IMCAL added as internal standard. The particulate mixture was dissolved by treatment with 2% SDS at 100° C. for 3 min and the resulting protein solution resolved by electrophoresis on a discontinuous (4%/12%) polyacrylamide slab gel. A small quantity of dansylated soybean trypsin inhibitor, molecular weight 21,500, was added to each sample in order to localize the IMCAL monomer by ultraviolet illumination. Separate lanes on each gel also contained up to 300 ng of IMCAL plus [$^{125}$I] IMCAL as external standards. The resolved proteins were transferred to nitrocellulose by electroblotting and the IMCAL monomer zone was excised from the nitrocellulose sheet and assayed both for $^{125}$I and for IMCAL by enzyme immunoassay. The latter procedure utilized rabbit antiserum to IMCAL monomer, peroxidase-conjugated goat anti-rabbit IgG as secondary antibody, and o-phenylenediamine as peroxidase substrate. The tissue content of IMCAL was calculated with reference to the external standards, using the recovery of [$^{125}$I] IMCAL in each lane to correct for differences in recovery between samples of the tissue particulate protein. As noted previously (18) the assay can detect 10 ng of IMCAL and is linear to at least 300 ng. Further, there is negligible reaction with the soluble calcium binding protein of Wasserman and Taylor (25) or with calmodulin derived from testis (CAABCO, Inc., Houston, Tex.).

Immunoassay with monoclonal antibody. The total particulate was fractionated to yield a membrane suspension enriched in IMCAL ("calcium binding complex") and this material was solubilized by treatment with 1-butanol, as previously described (17). The protein solutions were dialyzed against 30 volumes of 1.3 mM Tris of pH 7.4 containing 0.01% Triton X-100 (Sigma Chemical) for 36–48 h to remove traces of butanol, and aliquots containing 5-15 micrograms of protein were spotted on washed nitrocellulose disks for dot enzyme immunoassay (26). The disks were treated with the monoclonal antibody (RC2B6/1D1) followed by a peroxidaseconjugated goat anti-mouse IgG antibody (Boehringer Mannheim) and o-phenylenediamine as the enzyme substrate. The results were expressed as $OD_{492}$/min/mg protein for comparison purposes, inasmuch as the starting materials were butanol extracts rather than the completely solubilized particulates used for the polyclonal antiserum estimations. Accordingly, only the polyclonal assays provided estimates of the absolute content of IMCAL in tissue particulates.

yielded lower IMCAL values as compared to the control strains.

To determine whether the pattern of decreased tissue IMCAL is a consequence of the arterial hypertension, tissues of 4-5 week old rats were also compared and the results are shown in Table 2. Again, the mean values of the SHR samples were lower in erythrocyte ghosts (58.8-67.4% decrease), duodenal mucosa (30.8-43.8%), cecal mucosa (40.9-56.7%), kidney (16.7-31.8%) and testis (40.6-42.4%).

Results for the human experiment are shown in Table 3. In this case, rabbit polyclonal antiserum to rat IMCAL

TABLE 1

IMCAL content of total particulate fractions prepared from tissues of SHR, control Wistar Kyoto and Sherman strain rats aged 8-9 weeks.

| Tissue | No. of groups (determination)* | IMCAL content of total particulate (%) | | | P∓ | |
|---|---|---|---|---|---|---|
| | | SHR | Wistar Kyoto | Sherman | SHR versus Wistar Kyoto | SHR versus Sherman |
| Erythrocyte ghosts | 5 (8) | 0.18 ± 0.04 | 0.43 ± 0.07 | 0.43 ± 0.10 | <0.001 | <0.0125 |
| Duodenal mucosa | 5 (8) | 0.18 ± 0.02 | 0.29 ± 0.02 | 0.33 ± 0.06 | <0.01 | <0.05 |
| Jejunal mucosa | 4 (4) | 0.13 ± 0.05 | 0.24 ± 0.07 | 0.17 ± 0.05 | ns | ns |
| Cecal Mucosa | 5 (7) | 0.12 ± 0.02 | 0.21 ± 0.03 | 0.26 ± 0.04 | <0.005 | <0.0025 |
| Kidney | 5 (5) | 0.21 ± 0.06 | 0.39 ± 0.07 | 0.36 ± 0.07 | <0.05 | <0.025 |
| Heart | 5 (5) | 0.19 ± 0.06 | 0.46 ± 0.09 | 0.43 ± 0.08 | <0.0125 | <0.0125 |
| Testis | 5 (6) | 0.24 ± 0.03 | 0.43 ± 0.08 | 0.56 ± 0.18 | <0.025 | <0.05 |

*Five rate per group; animals weighed 161-195 g.
+Values listed are means ± SE. Total particulate preparations were solubilized with sodium dodecylsulfate and assayed with rabbit anti-rat IMCAL antisera as described in Materials and Methods. IMCAL content is expressed as a percentage (weight/weight) of the total particulate protein.
∓Calculated by Student's t-test of paired comparisons.

TABLE 2

IMCAL content of total particulate fractions prepared from tissues of SHR, Wistar Kyoto and Sherman strain rats aged 4-5 weeks.

| Tissue | No. of groups (determinations)* | IMCAL content of total particulate± | | | p∓ |
|---|---|---|---|---|---|
| | | SHR | Wistar Kyoto | Sherman | |
| Erythrocyte ghosts | 2 (3) | 0.14 ± 0.04 | 0.34 ± 0.06 | 0.43 ± 0.05 | <0.0025 |
| Duodenal mucosa | 2 (3) | 0.18 ± 0.03 | 0.26 ± 0.01 | 0.32 ± 0.01 | <0.01 |
| Cecal mucosa | 2 (3) | 0.13 ± 0.02 | 0.22 ± 0.06 | 0.30 ± 0.08 | <0.025 |
| Kidney | 2 (2) | 0.15 ± 0.07 | 0.18 ± 0.06 | 0.22 ± 0.07 | <0.0125 |
| Testis | 2 (2) | 0.19 ± 0.09 | 0.32 ± 0.17 | 0.33 ± 0.15 | <0.05 |

*Five rats (58-80 g) per group.
±Values are means ± SE. Assay method is described in Table 1 and Materials and Methods.
∓P values calculated by Student's t-test for paired comparisons of SHR versus Wistar Kyoto plus Sherman strain controls. Individual P values for t-tests of SHR versus Wistar Kyoto and Sherman rats, respectively, are <0.05 and <0.01 for erythrocyte ghosts and duodenal mucosa.

Results

Assays with polyclonal antiserum. Values of the IMCAL monomer content of tissues of SHR and control strain rats aged 8-9 weeks old are compared in Table 1. Significant reductions in the mean values of the SHR as compared to either the Wistar Kyoto or Sherman strain controls were observed in erythrocyte ghosts (58.1% decrease), duodenal mucosa (37.9-45.4%), cecal mucosa (42.9-53.8%), kidney (41.7%-46.2%), heart (55.8-58.7%) and testis (44.2-57.1%). A similar trend in the jejunal mucosal values did not reach statistical significance in 4 experiments. However, the jejunal values were significantly lower than those of the corresponding duodenal segments (P less than 0.02) in agreement with prior results (18). Calcium transport activity is greater in the duodenal as compared to the jejunal mucosa (20) and cecal mucosa also transports calcium readily (27). It is further noteworthy that in a few tests of spleen (N=3) and skeletal muscle (N=2) the SHR tissues consistently

TABLE 3

Assay of IMCAL in Erythrocyte Membranes of Normal Human Subjects and in 3 patients with Essential Hypertension
(1) Method: quantitative electroblotting with the rabbit polyclonal antiserum to rat IMCAL
(2) Results

| Subject | Status | IMCAL content (% of total membrane protein) |
|---|---|---|
| 1 | normal | 0.38 |
| 2 | normal | 0.27 |
| 3 | normal | 0.92 |
| 4 | patient | 0.44 |
| 5 | patient | 0.21 |
| 6 | patient | 0.20 |

IMCAL was directed toward human erythrocyte membrane. A reduction in IMCAL content of erythrocyte membranes of human subjects with essential hypertension is clearly shown related to normal subjects.

Assays with the monoclonal antibody. The values in Table 4 demonstrate significant reductions of immunoreactive IMCAL in SHR as compared to Wistar Kyoto tissues tested with monoclonal antibody. The decrease were observed in duodenal mucosa (40% reduction), jejunal mucosa (52.8%), cecal mucosa (37.6%), heart (40.3%), kidney (39.1%), and liver (18.2%); a trend in the same direction was observed in skeletal muscle (29.9% reduction; 0.05 less than P less than 0.1).

Discussion

The results indicate that decreases in the content of immunoreactive IMCAL in SHR tissues can account at least partially for the reductions in calcium binding reported by prior investigators. Devynck et al. (15), for example, observed decreased calcium binding capacity of the plasma membranes of four different SHR tissues and suggested that the syndrome involves an abnormality of a "ubiquitous membrane component." They reported an increment of 0.30 nmol/mg protein in the calcium binding capacity of erythrocyte vesicles prepared from Wistar Kyoto controls as compared to SHR. A comparable increment of 0.35 nmol/mg protein in the calcium binding capacity of erythrocyte membranes prepared from normal human subjects as compared to patients with essential hypertension is indicated by the results of Orlov and Postnov (28). From the values listed in Table 1, on the other hand, and from the monomer molecular weight of IMCAL we calculate an average increment of 0.22 nmols of IMCAL per mg membrane protein in erythrocyte ghosts of control rats as compared to SHR. Assuming one calcium ion bound in the membrane per IMCAL monomer, it is reasonable to suggest that the observed reduction in IMCAL content could account for much of the decrease in calcium binding. The finding, moreover, that the decrease in IMCAL content is present in 4-5 week old SHR, who have not yet developed hypertension, agrees with prior observations of reduced calcium binding at 3 weeks of age (15) and suggests that the IMCAL alteration may not be secondary to the elevated pressure.

The question arises whether a genetic change in SHR influences tissue IMCAL content directly, e.g., by alteration of a structural gene which encodes the protein, or whether the relationship is less direct. Inasmuch as IMCAL levels are subject to regulation by vitamin D and dietary calcium (17, 18), it is conceivable that a primary change in an enzyme or other component of a regulatory pathway could secondarily reduce the IMCAL content. Schedl et al. (29) have reported that calcium transport across the duodenal mucosa is decreased in SHR as compared to Wistar Kyoto controls, in accord both with the changes in duodenal IMCAL content shown in Tables 1 and 2 and with the hypothesis that IMCAL participates in the regulation of calcium translocation (17, 18). These authors, moreover, suggest the possibility of a defect in vitamin D metabolism in SHR, since the serum concentration of 1,25-dihyroxy vitamin D was not elevated in the face of depressed intestinal absorption of calcium and of increased immunoreactive parathyroid hormone in the plasma While the precise mechanism of the decrease in IMCAL content and the functional consequences of the reduction remain to be determined, the demonstration of the protein abnormality in SHR opens new avenues for the investigation of the animal syndrome and of essential hypertension in man.

References

1. Okamoto, K. & Aoki, K. (1963) *Jap. Cir. J.* 27, 282-293.
2. Postonov, Y. V., Orlov, S. N. & Pokudin, N. I. (1979) *Pflugers Archiv* 379, 191-195.
3. Montenay-Garestier, T., Aragon, I., Devynck, M. -A., Meyer, P. & Helen, C. (1981) *Biochem. Biophys. Res. Commun.* 100, 660-665.
4. Orlov, S. N., Gulak, P. V., Litvinov, I. S. & Postnov, Y. V. (1982) *Clin. Sci.* 63, 43-45.

Enzyme immunoassay with a mouse monoclonal antibody of the IMCAL content of butanol-extracted particulates prepared from tissues of SHR and Wistar Kyoto strain rats.

| Tissue | No. of groups (determinations)* | IMCAL immunoassay± ($OD_{492}$/min/mg protein) | | P+ |
|---|---|---|---|---|
| | | SHR | Wistar Kyoto | |
| Duodenal mucosa | 3 (3) | 15.3 ± 3.0 | 25.5 ± 2.8 | <0.05 |
| Jejunal mucosa | 3 (5) | 7.5 ± 2.2 | 15.9 ± 5.1 | <0.025 |
| Cecal mucosa | 3 (5) | 1.66 ± 0.40 | 2.66 ± 0.58 | <0.025 |
| Heart | 4 (6) | 1.05 ± 0.12 | 1.76 ± 0.23 | <0.025 |
| Kidney | 4 (6) | 1.40 ± 0.06 | 2.30 ± 0.36 | <0.025 |
| Liver | 4 (4) | 1.71 ± 0.58 | 2.09 ± 0.62 | <0.05 |
| Skeletal muscle | 3 (3) | 1.43 ± 0.43 | 2.04 ± 0.71 | $0.05 < P < 0.1$ |

*Five rate (aged 8-9 weeks) per group.
±Butanol extracts of total tissue particulates or of the calcium-binding complex fractions were assayed as described (Materials and Methods). The values (means ± SE, expressed in $OD_{492}$ units) are not directly comparable, therefore, to the SDS-solubilized preparations assayed in TABLES 1 and 2, which provide absolute estimates of tissue IMCAL content.
+P calculated by Student's t-tests of paired comparisons.

increment of 0.22 nmols of IMCAL per mg membrane protein in erythrocyte ghosts of control rats as compared to SHR. Assuming one calcium ion bound in the membrane per IMCAL monomer, it is reasonable to suggest that the observed reduction in IMCAL content could account for much of the decrease in calcium binding. The finding, moreover, that the decrease in IMCAL content is present in 4-5 week old SHR, who have not yet developed hypertension, agrees with prior observations of reduced calcium binding at 3 weeks of 5. Orlov, S. N., Gulak, P. V. & Postnov, Y. V. (1982) *Clin. Sci.* 63, 281-284.
6. Aoki K., Yamashita, K., Tomita, N., Tazumi, K. & Hotta, K. (1974) *Jap. Heart. J.* 15, 180-181.
7. Moore, L., Hurwitz, L., Davenport, G. R. & Landon, E. J. (1975) *Biochim. Biophys. Acta* 413, 432-443.
8. Mangelsen, E.L. & Bohr, D.F. (1975) *Physiologist* 18, 302.
9. Webb, R.C. & Bhalla, R.C. (1976) *J. Mol. Cell. Cardiol.* 8, 651-661.

10. Wei, J. -W., Janis, R. A. & Daniel, E. E. (1976) *Circ. Res.* 39, 133–140.
11. Bhalla, R. C., Webb, R. C., Singh, D., Ashley, T. & Brock, T. (1978) *Mol. Pharmacol.* 14, 468–477.
12. Kwan, C. -Y., Belbeck, L. & Daniel, E. E (1980) *Mol. Pharmacol.* 17, 137–140.
13. Devynck, M. -A., Pernollet, M. -G., Nunez, A. -M., & Meyer, P. (1981) *Clin. Exp. Hypertension* 3, 797–807.
14. Devynck, M. -A., Pernollet, M. -G., Nunez, A. -M. & Meyer, P. (1981) *Hypertension* 3, 397–403.
15. Devynck, M. -A., Pernollet, M. -G., Nunez, A. -M., Aragon, I., Montenay-Garestier, T., Helene, C. & Meyer, P. (1982) *Proc. Natl. Acad. Sci. U.S.A.* 79, 5057–5060.
16. Erne, P., Bolli, P., Burgisser, E. & Buhler, F. R. (1984) *N. Engl. J. Med.* 310, 1084–1088.
17. Kowarski, S. & Schachter, D. (1980) *J. Biol. Chem.* 255, 10834–10840.
18. Schachter, D. & Kowarski, S. (1983) in: *Calcium in Biological Systems*, eds. Rubin, R. P., Weiss, G. & Putney, J. W. (Plenum, New York), pp. 513–518.
19. Kowarski, S., Cowen, L. A., Takahashi, M. R. & Schachter, D. (1984) *Fed. Proc.* 43, 985.
20. Kowarski, S. & Schachter, D. (1975) *Am. J. Physiol.* 229, 1198–1204.
21. Abbott, R. E. & Schachter, D. (1976) *Analyt. Biochem.* 63, 414–417.
22. Wang, C. -S. & Smith, R. L. (1975) *Analyt. Biochem.* 63, 414–417.
23. Tjian, R., Stinchcomb, D., & Losick, R. (1974) *J. Biol. Chem.* 250, 8824–8828.
24. Towbin, H., Staehelin, T. & Gordon, J. (1979) *Proc. Natl. Acad. Sci. U.S.A.* 76, 4350–4354.
25. Wasserman, R. H. & Taylor, A. N. (1966) *Science* 152, 791–793.
26. Hawkes, R., Niday, E. & Gordon, J. (1982) *Anal. Biochem.* 119, 142–147.
27. Nellans, H. N. & Goldsmith, R. S. (1981) *Am. J. Physiol.* 240, G424–G431.
28. Orlov, S. N. & Postnov, Y. V. (1982) *Clin. Sci.* 63, 281–284.
29. Schedl, H. P., Miller, D. L., Pape, J. M., Horst, R. L. & Wilson, H. D. (1984) *J. Clin. Invest.* 73, 980–986.

What is claimed is:

1. A diagnostic method for identifying an individual predisposed to essential hypertension which comprises determining the amount of an integral membrane, calcium-binding protein present in a sample of a tissue from the individual, the integral-membrane, calcium-binding protein having a molecular weight of about 200,000 daltons in non-denaturing detergents and of about 20,500 daltons in sodium dodecyl sulfate polyacrylamide gels, a blocked amino terminus, an isoelectric point of about 4.5 and an affinity constant for the complexation of calcium of about 2.4 micromolar, and comparing the amount so determined with the amount of such protein present in a sample of the same tissue from a normal individual, a reduced amount being indicative of predisposition to essential hypertension.

2. A method of claim 1, wherein the tissue is erythrocyte membrane.
3. A method of claim 1, wherein the tissue is placenta.
4. A method of claim 1, wherein the tissue is intestine.
5. A method of claim 1, wherein the tissue is kidney.
6. A method of claim 1, wherein the tissue is bone.
7. A method of claim 1, wherein the tissue is brain.
8. A method of claim 1, wherein the tissue is heart.
9. A method of claim 1, wherein the tissue is testis.
10. A method of claim 1, wherein the tissue is spleen.
11. A method of claim 1, wherein the tissue is skeletal muscle.
12. A method of claim 1, wherein the tissue is liver.
13. A method of claim 1, wherein the detecting comprises autoradiography.
14. A method of claim 1, wherein the detecting comprises colorimetry.
15. A method of claim 1, wherein the monoclonal antibody is bound to a tube.
16. A method of claim 1, wherein the monoclonal antibody is bound to a bead.
17. The method of claim 1, wherein the determining comprises isolating a sample of tissue from the individual, treating the sample of tissue so as to obtain the integral membrane proteins present in the sample, contacting the proteins thus obtained with a monoclonal antibody directed against the integral-membrane calcium-binding protein under conditions permitting formation of a complex between the monoclonal antibody and the integral membrane calcium-binding protein to which it is directed, quantitatively determining the amount of complex so formed, and thereby the amount of the integral membrane calcium binding protein present in the sample.
18. A method of claim 17, wherein the monoclonal antibody is RC2B6/1D1 produced by hybridona cell line ATCC No. HB 9317.
19. A method of claim 1, wherein the monoclonal antibody is bound to a matrix.
20. A method of claim 19, wherein the matrix is agarose.
21. A method of claim 19, wherein the matrix is sepharose.
22. A method of claim 1, wherein the monoclonal antibody is labelled with a detectable marker.
23. A method of claim 22, wherein the detectable marker is a colorimetric marker.
24. A method of claim 22, wherein the detectable marker is the product of an enzymatic reaction.
25. A method of claim 22, wherein the detectable marker is a radioactive label.
26. A method of claim 25, wherein the radioactive label is $^{125}I$.
27. A method of claim 1, further comprising contacting any complex formed between the monoclonal antibody and the internal membrane, calcium-binding protein indicative of predisposition to essential hypertension with a second antibody molecule labelled with a detectable marker to form a second complex, and detecting the presence of the second complex.
28. A method of claim 27, wherein the detectable marker is a colorimetric marker.
29. A method of claim 27, wherein the detecting comprises autoradiography.
30. A method of claim 27, wherein the detecting comprises colorimetry.
31. A method of claim 27, wherein the detectable marker is the product of an enzymatic reaction.
32. A method of claim 31, wherein the detectable marker is a radioactive label.
33. A method of claim 32, wherein the radioactive label is $^{125}I$.
34. A method for quantitatively determining in a human subject the amount of an integral membrane calcium-binding protein indicative of predisposition to essential hypertension, and thereby determining the predisposition of the subject to essential hypertension, which comprises isolating a sample of the tissue from the subject, treating the sample of tissue so as to obtain the integral membrane proteins present in the sample, contacting the proteins thus obtained with a monoclonal antibody directed against the integral membrane calcium-binding protein under conditions permitting formation of a complex between the monoclonal antibody and the integral membrane calcium-binding protein to which it is directed to form a protein-antibody complex and quantitatively determining the amount of complex, a reduced amount relative to a normal subject being indicative of predisposition to essential hypertension.

* * * * *

UNITED STATES PATENT AND TRADEMARK OFFICE
CERTIFICATE OF CORRECTION

PATENT NO. : 4,840,894
DATED : June 20, 1989
INVENTOR(S) : David Schachter, et al.

It is certified that error appears in the above-identified patent and that said Letters Patent is hereby corrected as shown below:

In column 1, line 60, "secondar hypertension" should read --secondary hypertension--.

In column 2, line 45, "proteinis" should read --protein is--.

In column 3, line 12, "deweight of about 200,000 dalt tergents" should read --detergents--.

In column 3, line 26, "thepprotein" should read --the protein--.

In column 4, line 20, "cal- cium-binding should read --calcium-binding--.

In column 6, line 50, "wit the" should read --with--.

In column 6, line 56, "obt ained" should read --obtained--.

In column 6, line 58, "protein anti" should read --protein-anti--.

In column 7, line 59, after "individual", insert --i.e.,--.

In column 9, line 66, "2-weeks" should read --2-3 weeks--.

UNITED STATES PATENT AND TRADEMARK OFFICE
CERTIFICATE OF CORRECTION

PATENT NO. : 4,840,894

DATED : June 20, 1989

INVENTOR(S) : David Schachter, et al.

It is certified that error appears in the above-identified patent and that said Letters Patent is hereby corrected as shown below:

In column 10, line 20, "acetatecitrate" should read —acetate-citrate—.

In column 10, line 30, "125I" should read —$^{125}$I—.

In column 11, line 5, "peroxidaseconjugated" should read —peroxidase-conjugated—.

In column 12, line 13, delete "IMCAL".

In column 13, below line 40, insert —TABLE 4— above the table presented.

In column 13, delete lines 60-69.

In column 14, delete lines 1-2.

In column 14, line 22, "plasma While" should read —plasma. While—.

In claim 15, at column 16, line 9, "claim 1" should read —claim 17—.

In claim 16, at column 16, line 11 "claim 1" should read —claim 17—.

In claim 19, at column 16, line 29 "claim 1" should read —claim 17—.

In claim 22, at column 16, line 35, "claim 1" should read —claim 17—.

In claim 27, at column 16, line 45, "claim 1" should read —claim 17—.

Signed and Sealed this

Twenty-seventh Day of April, 1993

Attest:

MICHAEL K. KIRK

*Attesting Officer*   Acting Commissioner of Patents and Trademarks